United States Patent [19]
Chenard

[11] Patent Number: 5,852,040
[45] Date of Patent: Dec. 22, 1998

[54] NEUROPROTECTIVE 3,4-DIHYDRO-2(1H)-QUINOLONE COMPOUNDS

[75] Inventor: Bertrand Leo Chenard, Waterford, Conn.

[73] Assignee: Pfizer Inc., New York, N.Y.

[21] Appl. No.: 416,804

[22] PCT Filed: Jul. 23, 1993

[86] PCT No.: PCT/US93/06827

§ 371 Date: Apr. 25, 1995

§ 102(e) Date: Apr. 25, 1995

[87] PCT Pub. No.: WO94/10166

PCT Pub. Date: May 11, 1994

Related U.S. Application Data

[63] Continuation of Ser. No. 969,642, Oct. 30, 1992, abandoned.

[51] Int. Cl.$^6$ .......................... A61K 31/47; C07D 401/06
[52] U.S. Cl. ............................................. 514/312; 546/158
[58] Field of Search ............................... 546/158; 514/312

[56] References Cited

U.S. PATENT DOCUMENTS

| | | | |
|---|---|---|---|
| 3,509,164 | 4/1970 | Carron et al. | 546/240 |
| 5,034,401 | 7/1991 | Frost et al. | 514/323 |
| 5,306,723 | 4/1994 | Chenard | 514/304 |
| 5,498,610 | 3/1996 | Chenard | 514/227.8 |
| 5,506,231 | 4/1996 | Lipton | 514/289 |

FOREIGN PATENT DOCUMENTS

| | | |
|---|---|---|
| 0109317 | 5/1984 | European Pat. Off. |
| 0322361 | 12/1987 | European Pat. Off. |
| 0398578 | 11/1990 | European Pat. Off. |
| 0524846 | 1/1993 | European Pat. Off. |
| 2546166 | 11/1984 | France. |
| 51-118772 | 10/1976 | Japan. |
| 91/17156 | 11/1991 | WIPO. |
| 9117156 | 11/1991 | WIPO. |
| 9302052 | 2/1993 | WIPO. |

OTHER PUBLICATIONS

Bonte et al., J. Med. Chem., 25(4), pp. 361–368 (1990).
Carron et al., Arneim–Forsch., 21, pp. 1992–1998 (1971).
Gotti et al., J. Pharmacol. Exp. Therap., 247, pp. 1211–1222 (1988).
Carter et al., J. Pharmacol. Exp. Therap., 247, pp. 1222–1232 (1988).
Shalaby et al., J. Pharm. Exp. Ther., 1992, 260, pp. 925–932.
Mehta et al., Life Sciences, 1990, 46, pp. 37–42.
Schmidt et al., Pharm. Biochem. and Behavior, 1989, 32, pp. 621–623.
Wroblewski et al., Proc. Soc. Exp. Biol. Med., 1955, 90, pp.210–213.
Olney, Drug. Dev. Res., 1989, 17, pp. 299–319.
Meldrum, Clinical Sci., 1985, 68, pp. 113–122.
CA86: 198738m, 1977.
CA89: 43498y; Derwent 14858A, 1978.
CA89: 146938w; Derwent 48671A, 1978.
Chenard, Chemical Abstracts, vol. 116, 1991, Col. 116:83552u.
Riederer et al., Arzneim.–Forsch./Drug Res. 42 (l), Nr. 2a (1992), pp. 265–268.

*Primary Examiner*—C. Warren Ivy
*Assistant Examiner*—D.Margaret M. Mach
*Attorney, Agent, or Firm*—Peter C. Richardson; Paul H. Ginsburg; B. Timothy Creagan

[57] ABSTRACT

The present invention is directed to compounds of formula (I), and the pharmaceutically acceptable acid addition salts thereof, wherein R is selected from the group consisting of F, —$CF_3$, —$OCH_3$, —O($C_1$)alkyl substituted with 1 to 3 fluoro atoms. —O($C_2$) substituted with 1 to 5 fluoro atoms, and —O($C_3$)alkyl substituted with 1 to 7 fluoro atoms. The compounds of formula (I) are useful in the treatment of stroke, traumatic brain injury and central nervous system degenerative diseases.

15 Claims, No Drawings

NEUROPROTECTIVE 3,4-DIHYDRO-2(1H)-QUINOLONE COMPOUNDS

CROSS REFERENCE TO RELATED APPLICATIONS

This application is the national stage of PCT application number PCT/US93/06827 having an international filing date of Jul. 23, 1993, which is a continuation of U.S. application Ser. No. 07/969,642, filed Oct. 30, 1992, now abandoned.

BACKGROUND OF THE INVENTION

The present invention is directed to neuroprotective (excitatory amino acid receptor blocking) 6-[2-(4-hydroxy-4-phenylpiperidino)-1-hydroxypropyl]-3, 4 dihydro-2 (1H)-quinolone compounds, defined by the formula I below; the optical isomers of compounds of formula I; pharmaceutically acceptable salts thereof; pharmaceutical compositions comprising a compound of formula I; and a method of using these compounds in the treatment of stroke, addiction, pain, epilepsy, psychosis, traumatic brain injury resulting from such things as drowning, traumatic head injury, cardiac arrest, cardiac surgery or neurosurgical procedures or CNS degenerative diseases such as senile dementia of the Alzheimer's type, multiinfarct dementia, Huntington's disease, AIDS dementia, amyotropic lateral sclerosis and Parkinson's disease.

Glutamate is recognized as a major excitatory neurotransmitter in the human central nervous system. It has also been demonstrated that exposure of neuronal cells to excessive amounts of glutamate is neurotoxic. Thus conditions which can lead to excessive glutamate release (traumatic brain injury, epilepsy, Parkinson's disease, senile dementia of the Alzheimer's type, ischemia etc.) can lead to neurodegeneration. Therefore agents which can block glutamate receptors afford protection against these diseases and conditions. This excitotoxin hypothesis and the potential utilities for excitatory amino acid receptor antagonists is well known in the art and has been described in the literature (see for example: Olney, Drug Dev. Res.,1989, 17, 299. Meldrum, Clinical Sci., 1985, 68, 113).

Ifenprodil is a racemic, so-called dl-erythro compound having the relative stereochemical formula

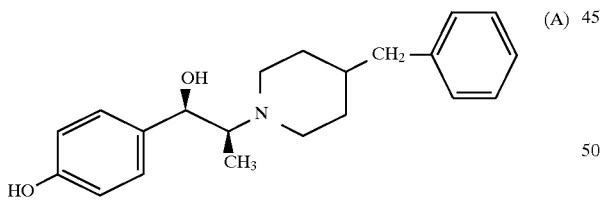

(A)

which is marketed as a hypotensive agent, a utility shared by a number of close analogs; Carron et al., U.S. Pat. No. 3,509,164; Carron et al., Drug Res., v. 21, pp.1992–1999 (1971). Ifenprodil has also been shown to possess antiischemic and excitatory amino acid receptor blocking activity; Gotti et al., J. Pharm. Exp. Therap., v.247, pp.1211–21 (1988); Carter et al., loc. cit., pp. 1222–32 (1988). See also published European patent application 322,361 and French Patent 2,546,166. A goal, substantially met by the present invention, has been to find compounds possessing such neuroprotective effect in good measure, while at the same time having lowered or no significant hypotensive effect.

Certain structurally related 1-phenyl-3-(4-aryl-4-acyloxypiperidino)-1-propanols have also been reported to be useful as analgesics, U.S. Pat. No. 3,294,804; and 1-[4-(amino- and hydroxy-alkyl)phenyl]-2-(4-hydroxy-4-tolylpiperazino)-1-alkanols and alkanones have been reported to possess analgesic, antihypertensive, psychotropic or antiinflammatory activity, Japanese Kokai 53-02,474 (CA 89:43498y; Derwent Abs. 14858A) and 53-59,675 (CA 89:146938w; Derwent Abs. 48671A).

More recently, in published European Patent Application No. 351,282, compounds which include those of the formula

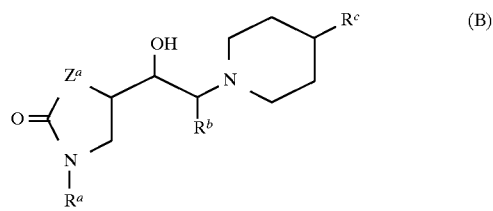

(B)

wherein $R^a$ and $R^b$ are each independently hydrogen or $(C_1-C_3)$alkyl, $R^c$ is benzyl, phenoxy, benzyloxy or phenoxymethyl, and $Z^a$ is $CH_2$, $C(CH_3)_2$ or $CH_2CH_2$, have been reported as having neuroprotective type activity.

PCT Application 91-101470, published Nov. 14, 1991, discloses, inter alia, compounds of the formula

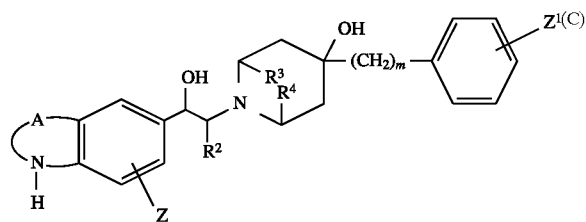

(C)

wherein A is

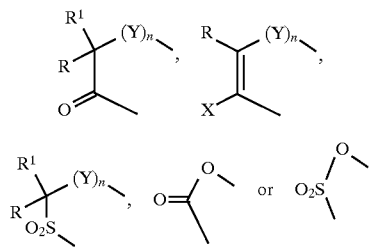

n is 0 or 1;

m is 0 or an integer from 1–6;

R, $R^1$ and $R^2$ are each independently hydrogen or $(C_{1-C_3})$ alkyl;

$R^3$ and $R^4$ are taken separately and are each hydrogen, or $R^3$ and $R^4$ are taken together and are ethylene;

X is hydrogen, $(C_1-C_3)$alkoxy or $[(C_1-C_3)$alkoxy] carbonyl;

Y is $CH_2$ or oxygen; and

Z and $Z^1$ are each independently hydrogen, $(C_{1-C_3})$alkyl, $(C_{1-C_3})$alkoxy, fluoro, chloro or bromo.

SUMMARY OF THE INVENTION

The present invention is directed to the racemic mixtures and enantiomerically pure compounds of the formula

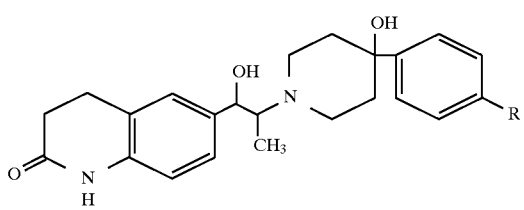

and the pharmaceutically-acceptable acid addition salts thereof wherein R is selected from the group consisting of F, —CF$_3$, —OCH$_3$, —O(C$_1$)alkyl substituted with 1 to 3 fluoro atoms, —O(C$_2$)alkyl substituted with 1 to 5 fluoro atoms and —O(C$_3$)alkyl substituted with 1 to 7 fluoro atoms.

The preferred compounds of the present invention are those of formula I wherein R is F, —CF$_3$ or —OCH$_3$. The preferred stereochemistry of the 1-hydroxypropyl central portion of the molecule is depicted as either

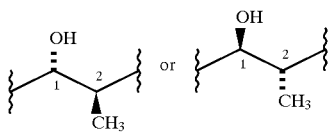

and which is specified as either (1S*, 2S*) or (1R*, 2R*).

The present invention is further directed to pharmaceutical compositions comprising a compound of formula I, and to methods of treating stroke, addiction, pain, epilepsy, psychosis, traumatic brain injury resulting from such things as drowning, traumatic head injury, cardiac arrest, cardiac surgery or neurosurgical procedures or CNS degenerative diseases such as senile dementia of the Alzheimer's type, multiinfarct dementia, Huntington's disease, AIDS dementia, amyotropic lateral sclerosis and Parkinson's disease with a compound of the formula I. The compounds and the pharmaceutically acceptable salts thereof according to the invention are of particular usefulness in said methods due to their unexpected efficacy upon oral administration.

The expression "pharmaceutically-acceptable acid addition salts" is intended to include but is not limited to such salts as the hydrochloride, hydrobromide, hydroiodide, nitrate, hydrogen sulfate, mandelate, dihydrogen phosphate, mesylate, maleate and succinate salts. Such salts are conventionally prepared by reacting the free base form of a compound of formula I with an appropriate acid, usually one molar equivalent, in a solvent. Those salts which do not precipitate directly are generally isolated by concentration of the solvent and/or addition of a non-solvent.

It will be noted that compounds of the formula I possess an asymmetric C-1 carbon and a second asymmetric center at the C-2 carbon of the alkanol. It will be evident to those skilled in the art of organic chemistry, therefore, that such compounds can be resolved into optical isomers showing equal but opposite rotation of plane polarized light. For example, all of these compounds are potentially resolved by fractional crystallization of their diastereomeric addition salts with an optically active acid, as exemplified below. The alcohols are also potentially resolved by chromatography or fractional crystallization of esters or urethanes derived by reaction with activated forms of optically active acids or with optically active isocyanates. Thus, the present invention should not be construed as limited to the racemic forms of the present compounds but includes the individual isomers thereof.

DETAILED DESCRIPTION OF THE INVENTION

The compounds of the present invention, having the formula I defined above, are readily prepared. The starting materials and reagents required for the synthesis of the compounds of the present invention are readily available, either commercially, according to literature methods, or by methods analogous to those exemplified in Preparations below.

As used herein, the expression "reaction inert solvent" refers to any solvent which does not interact with starting materials, reagents, intermediates or products in a manner which adversely affects the reaction or yield of the desired product.

The precursor ketones are generally prepared by nucleophilic displacement of an appropriately substituted 2-halo, 2-alkanesulfonyloxy- or 2-arylsulfonyloxy-1-alkanone with an appropriately substituted piperidine derivative, e.g.,

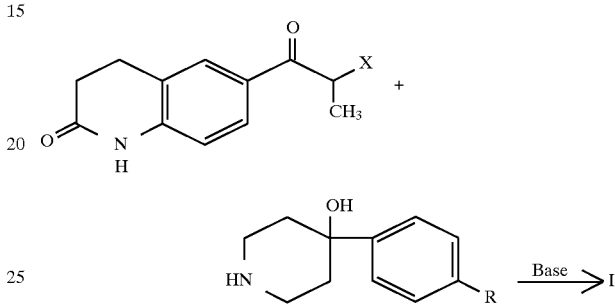

wherein X is typically chloro, bromo, mesyloxy or tosyloxy and R is as defined above. This reaction is carried out under conditions typical of nucleophilic displacements in general. Where the two reactants are about equivalent in availability, substantially molar equivalents may be used; although when one is more readily available, it is usually preferred to use that one in excess, in order to force this bimolecular reaction to completion in a shorter period of time. The reaction is generally carried out in the presence of at least 1 molar equivalent of a base, the piperidine derivative itself, if it is readily available, but more usually a tertiary amine which is at least comparable in base strength to the nucleophilic piperidine; and in a reaction inert solvent such as ethanol. If desired, the reaction is catalyzed by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 50°–120° C. is generally satisfactory. Conveniently, the temperature can be the reflux temperature of the reaction mixture.

The resulting ketone intermediates are conveniently converted to corresponding alcohols by conventional reduction with NaBH$_4$, usually in excess, in a protic solvent such as methanol or ethanol, generally at temperature in the range of about 15°–45° C.

The final product having the formula I can be converted from its free base form to a pharmaceutically acceptable salt form by conventional methods known in the art. For example, the formation of the mesylate salt is a typical procedure and is carried out as follows. The free base of a compound having the formula I is mixed with methane sulfonic acid in methanol. The solvent is removed and the residue is triturated with ethanol/ether to yield the mesylate salt as either crystals or a solid.

The compounds of formula I, as described hereinabove, can be separated into pure enantiomers, which have the absolute stereochemistry of either 1S,2S or 1R,2R at the optically active centers. A typical resolution technique is illustrated by the following method where the compound of formula I wherein R is F was separated into its two enantiomers. A mixture of the enantiomers in its free-base form, is mixed in a large amount of methyl ethyl ketone with either (S)-(+)-mandelic acid or (R)-(−)-mandelic acid. When the (S)-(+)-mandelic acid is used, the 1R,2R isomer is isolated and when the (R)-(−)-mandelic acid is used, the 1S,2S isomer is isolated. The mixture is refluxed and filtered to remove any insoluble particulates. The mixture is then boiled down to a quarter of its original volume, and allowed to cool to room temperature. The resultant crystals are isolated by filtration. The crystals can be further purified by recrystallization in methyl ethyl ketone. Four more recrystallizations yielded the respective pure enantiomers. The mandelate salt of the enantiomerically pure compound of formula I is converted to its free base form by stirring it in a saturated sodium bicarbonate solution. The enantiomerically pure free base of the compound of formula I is then converted to its mesylate salt form by the method described hereinabove.

The present compounds of the formula I possess selective neuroprotective activity, based upon their ability to block excitatory amino acid receptors, while at the same time generally having lowered or no significant hypotensive activity. The neuroprotective and excitatory amino acid antagonist activity of the present compounds is determined according to known in vitro methods, for example Shalaby, Chenard, Prochniak and Butler, J. Pharm. Exp. Ther., 1992, 260, p. 925. Seventeen day fetal rat (CD, Charles River) hippocampal cells are cultured on PRIMARIA culture plates (Falcon Co., Lincoln Park, N. J., USA) for 2–3 weeks in serum containing culture medium (Minimum Essential Medium with non-essential amino acids, containing 2 mM glutamine, 21 mM glucose, penicillin/streptomycin [5000 units each], 10% fetal bovine [days 1–7], and horse serum [days 1–21]). Cells are either plated on 96 well microtiter plates at a density of 80,000 cells per well or on 24 well culture plates at a density of 250,000 cells per well. Cultures are grown at 37° C. in a humidified $CO_2$ tissue culture incubator containing 5% $CO_2$ and 95% air. Proliferation of non-neuronal cells is controlled by adding 20 $\mu$M uridine and 20 $\mu$M 5-fluoro-2-deoxyuridine (Sigma Chemical Co., St. Louis, Mo.) from day 6–8 of culture. Culture media is exchanged every 2–3 days with fresh stock.

The cultures are assessed for glutamate toxicity two to three weeks from initial plating. Culture media is removed and cultures rinsed twice with a controlled salt solution (CSS) (NaCl (120 mM); KCl (5.4 mM); $MgCl_2$ (0.8 mM); $CaCl_2$ (1.8 mM)); glucose (15 mM); and HEPES (25 mM, pH 7.4). Cultures are then exposed for 15 minutes (37° C.) to various concentrations of glutamate. Following this incubation, cultures are rinsed three times with glutamate-free CSS and twice with fresh culture medium without serum. The cultures are then incubated for 20–24 hours in serum free culture medium. Compounds are added 2 minutes before, and during the 15 minute exposure to glutamate. In some experiments, drugs are added at different times after the glutamate exposure and for the following 20–24 hours.

Cell viability is routinely assessed 20–24 hours following the excitotoxin exposure by measuring the activity of the cytosolic enzyme lactate dehydrogenase (LDH). LDH activity is determined from the culture medium of each of the 96 wells of the microtiter plates. A 50 $\mu$l sample of the media is added to an equal volume of sodium phosphate buffer (0.1M, pH 7.4) containing 1.32 mM sodium pyruvate, and 2.9 mM NADH. The 340 nm absorbance of the total reaction mixture for each of the 96 wells is monitored every 5 seconds for 2 minutes by an automated spectrophotometric microtiter plate reader (Molecular Devices; Menlo Park, Calif.). The rate of absorbance is automatically calculated by negative kinetics analysis according to the method of Wroblewski et al., Proc. Soc. Exp. Biol. Med., vol. 90, p. 210, 1955, using an IBM SOFTmax program (version 1.01; Molecular Devices) and is used as the index of LDH activity.

Morphological assessment of neuronal viability is determined using phase contrast microscopy. The 96-well culture plates do not permit good phase-contrast imagery, so cells cultured on 24-well plates are used for this purpose. Quantitatively, both culture platings are equally sensitive to glutamate toxicity, and display 2–3 fold increases in LDH activity 24 hours following exposure to 0.1–1.0 mM glutamate.

Haloperidol was purchased from Research Biochemicals Inc. (Natick, Mass.). Horse and fetal bovine serum were purchased from Hyclone (Logan, Utah). Culture medium, glutamine, and penicillin/streptomycin were purchased from Gibco Co. (Grand Island, N.Y.).

Neurotoxicity is quantified by measuring the activity of LDH present in the culture medium 20–24 hours after glutamate exposure. LDH activity in the culture media correlates with destruction and degeneration of neurons. Because actual levels of LDH vary from different cultures, data are routinely expressed relative to buffer-treated sister wells of the same culture plate. To obtain an index of LDH activity from glutamate and compound treated cultures, the LDH values from control cultures are subtracted from that of the treatment groups. Data for drug treatments are expressed as a percentage of the increase in LDH induced by 1 mM glutamate (or NMDA) for each experiment. Concentrations of NMDA antagonists required to reverse 50% of the LDH increase induced by excitotoxins ($IC_{50}$) are calculated using log-probit analysis from the pooled results of 3 independent experiments. Different treatment groups are compared using a two-tailed t-test.

An efficacious level of oral activity in a compound is important for many reasons including: allowance for a wider range of treatment forms; facilitation of the continuous dosages which are required over time for treating chronic disorders, such as Parkinson's disease, Alzheimer's disease, Huntington's Disease, etc.; and-avoidance of potential side-effects which would result from having to use higher dosages of a compound with a low degree of oral activity. The compounds of formula (I) are assayed for in vivo oral activity according to known methods, for example, Mehta, Ticku, Life Sciences, 1990, 46, pages 37–42 and Schmidt, Bubser, Pharmacology, Biochemistry and Behavior, 1989, 32, pages 621–623.

Male CD rats (150–170 g at arrival) are acclimated to the animal facility for approximately six days and are food deprived for 18 –24 hours prior to the experiment. Animals are housed 3 per box and taken to the test room. The animals are administered the test compound (sc or po) followed immediately by haloperidol (1 mg/Kg, sc). Typically, six animals are tested for each dose of compound along with a control group of six animals which receive only haloperidol. After thirty minutes, each rat is placed on a flat surface with its forepaws on a 1 cm bar which is 10 cm above the flat surface. The latency for the rat to remove its forepaws from the bar is a measure of catalepsy. Animals are observed for up to 30 seconds. The test is terminated at 30 seconds for any animal not responding by this time and the animal is given a test score of 30. The experimenter is blind to the doses of test compound. Data are analyzed nonparametrically using a Kruskall-Wallis test. $ED_{50}$'s are calculated using probit analysis.

Undesired hypotensive activity is also determined by known methods, for example, according to the methods of Carron et al., also cited above.

Such selective neuroprotective and excitatory amino acid blocking activities reflect the valuable utility of the present compounds in the treatment of stroke, traumatic brain injury and degenerative CNS (central nervous system) disorders such as senile dementia of the Alzheimer's type, amyotropic lateral sclerosis, Parkinson's disease and Huntington's disease, etc.; without significant potential for a concurrent, undue drop in blood pressure. In the systemic treatment of such diseases with a neuroprotective amount of compounds of the formula (I), the dosage is typically from about 0.02 to 10 mg/kg/day (1–500 mg/day in a typical human weighing 50 kg) in single or divided doses, regardless of the route of administration. Of course, depending upon the exact compound and the exact nature of the individual illness, doses outside this range may be prescribed by the attending physician. The oral route of administration is preferred. However, if the patient is unable to swallow, or oral absorption is otherwise impaired, the preferred route of administration will be parenteral (s.c., i.m., i.v.).

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

The present invention is illustrated by the following examples, but is not limited to the details thereof.

All non-aqueous reactions were run under a nitrogen atmosphere for convenience and to improve yields. All non-protic solvents were purchased dry (Aldrich Sure-Seal) or dried according to conventional procedures.

EXAMPLE 1

6-[2S*-(4-Hydroxy-4-(4-trifluoromethylphenyl) piperidino)-1 S*-hydroxypropyl]-3,4-dihydro-2(1H) -quinolone mesylate A mixture of 4-hydroxy -4-(4-trifluoromethylphenyl) piperidine (2.0 g, 8.16 mmol), 6-(2-chloropropionyl)-3,4-dihydro-2(1H)-quinolone (1.93 g, 8.12 mmol), and triethylamine (2.3 mL, 16.5 mmol) in ethanol (75 mL) was refluxed overnight (18 hours). The reaction was concentrated and the brown residue was stirred for 1.5 hours with 75 mL of water and 75 mL of ether. The tan solid which formed 6-[2S*-(4-hydroxy-4-(4-trifluoromethylphenyl)piperidino)-1S*-propionyl]-3, 4-dihydro-2(1H)-quinolone was collected, rinsed with ether and air dried (2.45 g, 67%). The product was of sufficient purity to be used directly in the next step. A sample recrystallized from ethanol/methylene chloride/ether was cream colored and had a mp of 201.5°–202.5° C. Analysis calculated for $C_{24}H_{25}F_3N_2O_3$: C, 64.57; H, 5.64; N, 6.27. Found: C, 64.13; H, 5.65; N, 6.16.

Sodium borohydride (0.17 g, 4.49 mmol) was partially dissolved in ethanol (50 mL) with stirring for 15 minutes. A solution of 6-[2S*-(4-hydroxy-4-(4-trifluoromethyl-phenyl) piperidino)-1S*-propionyl]-3,4-dihydro-2(1H)-quinolone (2.0 g, 4.48 mmol) in ethanol (200 mL) was added and the solution was stirred for 2 hours. Additional sodium borohydride (0.17 g) was added at this time and again after 4 hours. Stirring was continued overnight. Water (50 mL) was added and the reaction mixture was concentrated to a brown foam. Water (100 mL) and ether (100 mL) were added and a solid formed during 30 minutes of vigorous stirring. The solids were collected, rinsed with water and then ether, and air dried (1.33 g, 66%). The product was further purified by recrystallization from ethanol (0.72 g cream solid). The methane sulfonic acid salt was prepared from 0.5 g of 6-[2S*-(4-Hydroxy-4-(4-trifluoromethyl-phenyl) piperidino)-1S*-hydroxypropyl]-3,4-dihydro-2(1H)-quinolone and methane sulfonic acid (0.072 mL, 1.11 mmol) in methanol (15 mL). The solvent was removed and the residue was triturated with ethanol/ether to give 0.594 g of a gray-white solid which had mp 237°–238° C. Analysis calculated for $C_{24}H_{27}F_3N_2O_3$—$CH_4SO_3$—0.025 $H_2O$: C, 54.69; H, 5.78; N, 5.10. Found: C, 54.72; H, 5.73; N, 4.96.

EXAMPLE 2

6-[2S*-(4-Hydroxy-4-(4-methoxyphenyl)piperidino) -1S*-hydroxypropyl]-3, 4-dihydro-2(1H)-quinolone mesylate A mixture of 4-hydroxy-4-(4-methoxyphenyl)piperidine (2.1 g, 10.13 mmol), 6-(2-chloropropionyl)-3,4-dihydro-2 (1H)-quinolone (2.40 g, 10.1 mmol), and triethylamine (2.9 mL, 20.8 mmol) in ethanol (75 mL) was refluxed overnight (18 hours). Upon cooling, 2.35 g (57%) of 6-[2S*-(4-hydroxy-4-(4-methoxyphenyl)piperidino)-1S*-propionyl] -3, 4-dihydro-2(1H)-quinolone precipitated as a tan solid which was suitable for use in the next step. A sample recrystallized from ethanol/methylene chloride gave orange-brown needles and had a mp of 193.5°–197° C. Analysis calculated for $C_{24}H_{28}N_2O_4$—0.75 $H_2O$: C, 68.31; H, 7.05; N, 6.64. Found: C, 68.18; H, 6.70; N, 6.58.

Sodium borohydride (0.19 g, 5.02 mmol) was partially desolved in (50 mL) with stirring for 15 minutes. A solution of 6-[2S*-(4-hydroxy-4-(4-methoxyphenyl)-piperidino)-1 S*-propionyl]-3,4-dihydro-2(1H)-quinolone (2.0 g, 4.9 mmol) in ethanol (200 mL) was added and the solution was stirred for 2 hours. Additional sodium borohydride (0.17 g) was added at this time and again after 4 hours. Stirring was continued overnight. The product which precipitated during the reaction was collected and rinsed well with water and ether. Air drying afforded 1.51 g (75%) of the product as a tan solid. This material was recrystallized from ethanol to give 1.16 g of product in two crops. The methane sulfonic acid salt was prepared from 0.5 g of 6-[2S*-(4hydroxy-4-(4-methoxyphenyl)pipedino)-1S*-hydroxypropyl]-3,4-dihydro-2(1H)-quinolone and methane sulfonic acid (0.079 mL, 1.22 mmol) in methanol (20 mL). The solvent was removed and the residue was triturated with ethanol/ether to give 0.40 g of a white solid which had a mp of 212°–213° C. Analysis calculated for $C_{24}H_{30}N_2O_4$—$CH_4SO_3$: C, 59.27; H, 6.76; N, 5.53. Found: C, 59.19; H, 6.51; N, 5.42.

EXAMPLE 3

6-[2S*-(4-Hydroxy-4-(4-fluorophenyl)piperidino)- 1S*-hydroxypropyl]-3, 4-dihydro-2(1H)-quinolone mesylate A mixture of 4-hydroxy-4-(4-fluorophenyl)piperidine (41.8 g, 214 mmol), 6-(2-chloropropionyl)-3 ,4-dihydro-2 (1H)-quinolone (50.8 g, 214 mmol), and triethylamine (60 mL, 430 mmol) in ethanol (1200 mL) was refluxed 18 hours.

The reaction was cooled to 60° C. and filtered to remove a brown residue. The solvent was removed and the residue was vigorously stirred with 500 mL of water and 500 mL of ether. The solid which formed was collected and rinsed well with water and ether, then it was air dried to afford 59.4 g (70%) of 6-[2S*-(4-hydroxy-4-(4-fluorophenyl)piperidino)-1S*-propionyl]-3,4-dihydro-2(1H)-quinolone as a tan solid which was suitable for use in the next step. A sample recrystallized from methylene chloride/ether gave a tan solid and had a mp of 191°–192.5° C. Analysis calculated for $C_{23}H_{25}FN_2O_3$. 0.5 $H_2O$: C, 68.13; H, 6.46; N, 6.91. Found: C, 68.48; H, 6.24; N, 6.87.

The following reaction was carried out four times in side by side flasks and the combined reactions were then worked up together. Sodium borohydride (5.67 g, 150 mmol) was partially dissolved in ethanol (475 mL) with stirring for 15 minutes. A solution of 6-[2S*-(4 -hydroxy-4-(4-fluorophenyl)piperidino)-1S*-propionyl]-3, 4-dihydro-2 (1H)-quinolone (14.85 g, 37.5 mmol) in ethanol (700 mL) was added with a 700 mL rinse and the solution was stirred 23 hours. The product which precipitated during the four reactions was collected and air dried to give 31.6 g (58%) of the product as a tan solid which was suitable for mesylate salt formation. The methane sulfonic acid salt was prepared from 1.0 g of 6-[2S*-(4-hydroxy-4-(4-fluorophenyl) piperidino)-1S*-hydroxypropyl ]-3,4-dihydro-2(1H)-quinolone and methane sulfonic acid (0.163 mL, 2.51 mmol) in methanol (30 mL). The solvent was removed and the residue was recrystallized from ethanol/water to give 0.94 g of light tan solid which had a mp of 251°–252° C. Analysis calculated for $C_{23}H_{27}FN_2O_3$—$Ch_4SO_{3: C,}$ 58.28; H, 6.32; N, 5.66. Found: C, 58.36; H, 5.99; N, 5.59.

EXAMPLE 4

6-[2R-(4-Hydroxy-4-(4-fluorophenyl)piperidino)-1R-hydroxypropyl]-3, 4-dihydro-2(1H)-quinolone mesylate 6-[2S*-(4-Hydroxy-(4-fluorophenyl)piperidino)-1S*-hydroxypropyl]-3,4-dihydro-2(1H)-quinolone (18.0 g, 45.2 mmol) and (S)-(+)-mandelic acid (6.88 g, 45.2 mmol) were combined in methyl ethyl ketone (7 L). The mixture was heated to reflux and filtered to remove insoluble particulates. The solution was boiled down to 1800 mL and allowed to cool to room temperature and stand overnight. The orange-white crystals were collected, rinsed well with ether and dried to give 14.6 g. These crystals were recrystallized 5 more times from methyl ethyl ketone to yield 4.16 g of 6-[2R-(4-hydroxy-4--(4-fluorophenyl)piperidino)-1R-hydroxypropyl]-3,4-dihydro-2(1H)-quinolone (+) mandelate as light tan needles which had a mp of 224°–224.5° C.; $[\alpha]_D$=–12.60° (c=0.285 in methanol). Analysis calculated for $C_{23}H_2FN_{27}O_3$—$C_8H_8O_3$: C, 67.62; H, 6.41; N, 5.09. Found: C, 67.39; H, 6.02; N, 5.08.

6-[2R-(4-Hydroxy-4-(4-fluorophenyl)piperidino)-1R-hydroxypropyl]-3, 4-dihydro-2(1H)-quinolone free base was obtained from the above mandelate salt (4.06 g, 7.24 mmol) by stirring with saturated sodium bicarbonate (500 mL). The free base was filtered directly from the mixture, rinsed with water and air dried. The yield was 2.91 g (99%) of light tan solid: mp 243°–244° C.; $[\alpha]_D$=–44.60° (c=0.280 in methanol). Analysis calculated for $C_{23}H_{27}FN_2O_3$: C, 69.33; H, 6.83; N, 7.03. Found: C, 68.95; H, 6.55; N, 6.96.

6-[2R-(4-Hydroxy-4-(4-fluorophenyl)piperidino)-1R-hydroxypropyl]-3,4-dihydro-2(1H)-quinolone mesylate was prepared from the free base above (2.81 g, 7.05 mmol) and methane sulfonic acid (0.458 mL, 7.06 mmol) in methanol (100 mL). The solvent was removed and the residue was recrystallized from 95% ethanol to afford 3.10 g (89%, two crops) of the mesylate salt as a tan solid which had: mp 249.5°–250° C.; $[\alpha]_D$=–49.7° (c=0.290 in methanol). Analysis calculated for $C_{23}H_{27}FN_2O_3$—$CH_4SO_3$: C, 58.28; H, 6.32; N, 5.66. Found: C, 58.10; H, 6.26; N, 5.93.

EXAMPLE 5

6-[2S-(4-Hydroxy-4-(4-fluorophenyl)piperidino)-1S-hydroxypropyl]-3,4-dihydro-2(1H)-quinolone mesylate The title compound was prepared from 6-[2S*-(4-Hydroxy-4-(4-fluorophenyl)-piperidino)-1S*-hydroxypropyl]-3,4-dihydro-2(1H)-quinolone as described in Example 4 but substituting (R)-(–)-mandelic acid for the chiral acid. The free base, (–)-mandelate salt, and the mesylate salt all had identical physical properties to those cited in Example 4, except that the specific rotations were of the opposite sign. Listed below are the 3 products and their corresponding rotations.

| (–)Mandelate salt | $[\alpha]_D$ = +14.9° (c = 0.290 in methanol) |
|---|---|
| Free base | $[\alpha]_D$ = +45.9° (c = 0.275 in methanol) |
| Mesylate salt | $[\alpha]_D$ = +50.2° (c = 0.285 in methanol) |

Preparation 1

1-Benzyloxycarbonyl-4-piperidone

4-Piperidone hydrochloride hydrate (50.0 g, 325 mmol) and potassium bicarbonate (181.9 g, 1.82 mol) were combined in a two phase mixture of ethyl acetate (750 mL) and water (75 mL). Benzyl chloroformate (49 mL, 343 mmol) was added dropwise to the stirred mixture over 10 minutes. The mixture was stirred 2.5 hours, then it was diluted with water (700 mL) and the phases were separated. The aqueous layer was extracted with ethyl acetate and the combined organic phase was washed with water and brine. The organic phase was dried over magnesium sulfate and concentrated to a light yellow oil (76.75 g, 100%). The material was found to be analytically pure and suitable for further transformation without further workup. Analysis calculated for $C_{13}H_{15}NO_3$: C, 66.94; H, 6.48; N, 6.00. Found: C, 66.67; H, 6.48; N, 5.90.

Preparation 2

6-(2-Chloropropionyl)-3,4-dihydro-2(1H)-quinolone

Aluminum chloride (109 g, 817 mmol) was slurried in carbon disulfide (600 mL) and 2-chloropropionyl chloride (16.8 mL, 173.07 mmol) was added. To this mixture was added 3,4-dihydro-2(1H)-quinolone (20.0 g, 135.89 mmol, J. Amer. Chem. Soc., 1944, 66, 1442). The mixture was refluxed for 4 hours, cooled, and the carbon disulfide poured off and discarded. The reddish residue was carefully quenched with ice water which caused the product to solidify. The solids were collected, rinsed well with water, and suctioned dry followed by drying in vacuo. The product weighed 31.37 g (97%) and had mp 205°–206° C. Analysis calculated for $C_{12}H_{12}ClNO_2$: C, 60.64; H, 5.09; N, 5.89. Found: C, 60.20; H, 4.89; N, 5.78.

Preparation 3

4-Hydroxy(4-trifluoromethylphenyl)piperidine

4-Bromobenzotrifluoride (6.05 mL, 43.21 mmol) dissolved in ether (5 mL) was added dropwise over 10 minutes to magnesium turnings (1.25 g, 51.42 mmol). The mixture became mildly exothermic and turned red-brown while the Grignard reagent formed during 1.5 hours of stirring. The mixture was chilled with ice and 1-benzyloxycarbonyl-4-piperidone (10.0 g, 42.87 mmol dissolved in 50 mL of ether) was added dropwise over 10 minutes to the reaction. The reaction was allowed to warm to room temperature and stirred overnight. The mixture was quenched with saturated ammonium chloride and the phases were separated. The aqueous layer was further extracted with ether. The combined organic phase was washed with water and brine, dried over magnesium sulfate and concentrated. The residue was purified by flash chromatography on silica gel (3×6 inches, 30% ethyl acetate/hexane) to give 1-benzyloxycarbonyl4-hydroxy-4-(4-trifluoromethylphenyl)piperidine as an orange oily product which solidified on standing (12.48 g, 77%). The material was suitable for use in the next step. A sample recrystallized from ether/hexane had mp 102°–102.5° C. Analysis calculated for $C_{20}H_{20}F_3NO_3$: C, 63.32; H, 5.31; N, 3.69. Found: C, 63.25; H, 5.27; N, 3.71.

A mixture of 1-benzyloxycarbonyl-4-hydroxy-4-(4-trifluoromethylphenyl)-piperidine (12.3 g, 32.4 mmol), ethanol (150 mL), and 10% palladium on carbon (1.4 g) was hydrogenated in a Parr apparatus (initial hydrogen pressure was 48 psi). After 2.5 hours, the mixture was filtered through celite and concentrated. The residue was triturated with ether/hexane to obtain 4.98 g (63%) of 4-hydroxy-4-(4-trifluoromethylphenyl)-piperidine as a white solid which had mp 130.5°–132° C. Analysis calculated for $C_{12}H_{14}F_3NO$—$0.25\ H_2O$: C, 57.71; H, 5.85; N, 5.61. Found: C, 57.91; H 5.77; N, 5.54.

Preparation 4

4-Hydroxy4-(4-methoxyphenyl)-piperidine

The title product was prepared analogously to Preparation 3 starting with 4-bromoanisole. 1-Benzyloxycarbonyl-4-hydroxy-4-(4-methoxyphenyl)-piperidine was obtained in 31% yield and a sample recrystallized from ether/hexane was a white solid and had mp 96°–97.5° C. Analysis calculated for $C_{20}H_{23}NO_4$: C, 70.36; H, 6.79; N, 4.10. Found: C, 70.26; H, 6.28; N, 4.01. 4-Hydroxy-4-(4-methoxyphenyl)-piperidine was obtained as a white solid after ether/hexane trituration in 80% yield and had mp 120°–122° C. Analysis calculated for $C_{12}H_{17}NO_2$—$0.25\ H_2O$: C, 68.06; H, 8.33; N, 6.61. Found: C, 67.86; H, 8.21; N, 6.48.

Preparation 5

4-Hydroxy-4(4-fluorophenyl)-piperidine

The title product was prepared analogously to Preparation 3 starting with 4-bromofluorobenzene. 1-Benzyloxycarbonyl-4-hydroxy-4-(4-fluoro-phenyl)-piperidine was obtained in 82% yield and a sample recrystallized from ether/hexane was a white solid and had mp 86°–87° C. Analysis calculated for $C_{19}H_{20}FNO_3$—$0.25\ H_2O$: C, 68.35; H, 6.19; N, 4.20. Found: C, 68.69; H, 6.01; N, 4.26. 4-Hydroxy-4-(4fluorophenyl)-piperidine was obtained as a white solid after ether/hexane trituration in 99% yield-and is an item of commerce.

What is claimed is:

1. A compound having the formula I

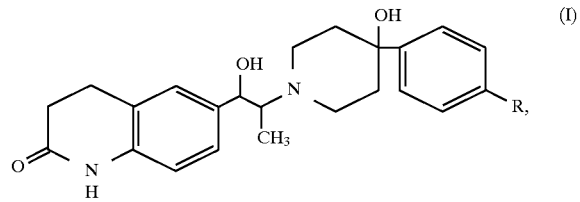

the optical isomers of compounds of formula I, and the pharmaceutically acceptable salts thereof wherein R is selected from the group consisting of $CF_3$, —$O(C_1)$ alkyl substituted by 1 to 3 fluoro atoms, —$O(C_2)$alkyl substituted by 1 to 5 fluoro atoms, and —$O(C_3)$alkyl substituted by 1 to 7 fluoro atoms.

2. A compound or a pharmaceutically acceptable salt thereof according to claim 1 having the absolute stereochemistry 1R,2R.

3. A compound or a pharmaceutically acceptable salt thereof according to claim 1 wherein R is —$CF_3$.

4. A compound or a pharmaceutically acceptable salt thereof according to claim 3 having the absolute stereochemistry 1R,2R.

5. A compound or a pharmaceutically acceptable salt thereof according to claim 3 having the absolute stereochemistry 1S,2S.

6. A compound or a pharmaceutically acceptable salt thereof according to claim 1 wherein R is —$OCF_3$.

7. A compound or a pharmaceutically acceptable salt thereof according to claim 6 having the absolute stereochemistry 1R,2R.

8. A compound or a pharmaceutically acceptable salt thereof according to claim 6 having the absolute stereochemistry 1S,2S.

9. A pharmaceutical composition comprising an amount of a compound or a pharmaceutically acceptable salt thereof according to claim 1 and a pharmaceutically acceptable diluent or vehicle.

10. A method of treating stroke, traumatic brain injury or a central nervous system degenerative disease in a mammal which comprises administering to said mammal an effective amount of a compound or a pharmaceutically acceptable salt thereof according to claim 1.

11. A method according to claim 10 wherein the compound or a pharmaceutically acceptable salt thereof is administered orally.

12. A method according to claim 10 wherein the compound or a pharmaceutically acceptable salt thereof is administered parenterally.

13. A method according to claim 10 wherein the central nervous system degenerative disease is Parkinson's disease, Huntington's disease, Alzheimer's disease or amyotropic lateral sclerosis.

14. A method according to claim 10 wherein traumatic brain injury is treated.

15. A method according to claim 10 wherein stroke is treated.

* * * * *